United States Patent [19]
Pilloud et al.

[11] Patent Number: 5,285,251
[45] Date of Patent: Feb. 8, 1994

[54] APPARATUS AND METHODS FOR OPTICAL EMISSION SPECTROSCOPY

[75] Inventors: Francis Pilloud, Clarens; Wilfried Vogel, Cully, both of Switzerland

[73] Assignee: Fisons plc, England

[21] Appl. No.: 512,792

[22] Filed: Apr. 23, 1990

[30] Foreign Application Priority Data

| Apr. 29, 1989 | [GB] | United Kingdom | 89/09920 |
| Apr. 29, 1989 | [GB] | United Kingdom | 89/09921 |
| Apr. 29, 1989 | [GB] | United Kingdom | 89/09922 |
| Apr. 29, 1989 | [GB] | United Kingdom | 89/09923 |

[51] Int. Cl.$^5$ .......................... G01J 3/30; G01N 21/67
[52] U.S. Cl. .................................................. 356/313
[58] Field of Search ............... 356/313, 315, 307; 315/240, 252; 219/130.32

[56] References Cited

U.S. PATENT DOCUMENTS

| 1,971,215 | 8/1934 | Feussner | 356/313 |
| 3,308,339 | 3/1967 | Berneron | 315/172 |
| 3,396,303 | 8/1968 | Gordon | 356/313 |
| 3,729,259 | 4/1973 | Cooper et al. | 356/307 |
| 4,055,783 | 10/1977 | Walters et al. | 356/313 |
| 4,824,249 | 4/1990 | Lucas et al. | 356/314 |

FOREIGN PATENT DOCUMENTS

| 0038549 | 10/1981 | European Pat. Off. . |
| 0318900 | 6/1989 | European Pat. Off. . |
| 833570 | 4/1960 | United Kingdom . |
| 1066431 | 4/1967 | United Kingdom . |

Primary Examiner—Vincent P. McGraw
Assistant Examiner—K. P. Hantis
Attorney, Agent, or Firm—Marshall, O'Toole, Gerstein, Murray & Borun

[57] ABSTRACT

A spark generator suitable for use in an optical emission spectrometer, and capable of generating a spark in a spark gap formed between an electrode and a sample to be analyzed, comprises a generator for generating a current of programmable amplitude in the spark gap in each of a series of discrete time intervals. The spark generator according to the invention is advantageous when compared with conventional spark generators in that it enables a higher degree of choice and control in the form of the spark. In particular, it enables the amplitudes of various portions of the spark to be independently varied, thus permitting the shape of the spark to be tailored to the particular analysis being performed. Also described are methods of optical emission spectroscopy which make use of the advantageous properties of the spark generator.

17 Claims, 5 Drawing Sheets

APPARATUS AND METHODS FOR OPTICAL EMISSION SPECTROSCOPY

FIELD OF THE INVENTION

This invention relates to optical emission spectroscopy, in particular to a spark generator for use in optical emission spectrometers and to methods of optical emission specroscopy using that spark generator.

BACKGROUND OF THE INVENTION

Optical emission spectroscopy involves exciting the chemical elements in a sample to emit light of one or more specific wavelengths (spectral light). The spectral light is generally produced by a short spark produced by a spark generator. Using conventional spark generators, in which sparks are generated by discharging a capacitor through a resistance and an inductance into the analytical gap, it is not possible to exercise a high degree of control over the waveform of the spark. This is due inter alia to the fact that the form of the spark is determined by the values of the capacitor C, resistance R and inductance L and also by the voltage V to which the capacitor is charged. In practice, therefore, the sparks which can be generated are limited by the availability of only fixed values of C, L, R and V.

SUMMARY OF THE INVENTION

We have now devised an improved form of spark generator for use in optical emission spectrometers which exhibits advantageous properties when compared with conventional spark generators.

Thus, according to the invention there is provided a spark generator suitable for use in an optical emission spectrometer, which comprises means for generating a current of programmable amplitude in each of a series of discrete time intervals.

The spark generator according to the invention is advantageous when compared with conventional spark generators in that it enables a higher degree of choice and control in the form of the spark. In particular, it enables the amplitudes of various portions of the spark to be independently varied, thus permitting the shape of the spark to be tailored to the particular analysis being performed. In addition, it is possible to choose a repetition rate independent of the mains supply frequency and to select a long lasting current with a short rise time. This is important because the dependence of the analysis on the physical or metallurgical properties of the sample depends inversely o the rise time of the spark; the peak current is mainly responsible for determining the evaporation of the sample (ie for the quantity of sample evaporated); and the currents at later times determine the excitation of the atoms in the vapour cloud.

Also, it is possible to create the discharge conditions in such a way that the waveform is unidirectional, ie such that there are no oscillations, without loss of energy, as occurs when resistance is added to a conventional circuit for the same purpose.

DETAILED DESCRIPTION OF THE INVENTION

The discrete time periods for which the current is programmable are preferably of from about 5 to 20 $\mu s$, eg 10 $\mu s$ or 12 $\mu s$, and the total duration of the spark is preferably from about 50 to 2000 $\mu s$.

The spectrometer including the spark generator is preferably provided with an electronic memory to store a number of programs defining spark waveforms appropriate for particular analytical applications. There is also preferably provided programming means to enable the user to generate a program defining a chosen form of spark.

The amplitude of the current at any particular time is preferably controlled by comparison with a reference current, which is preferably stored in the memory of a computer unit. Thus, the spark generator preferably includes means for measuring the instantaneous current flowing through the spark gap and means for adjusting that current to a predetermined value.

The means for measuring the current may be any conventional component known to be suitable for that purpose, eg a resistor. The means for adjusting the amplitude of the current may be a comparator connected to a switch, eg a transistor, so as to open the switch if the current increases above its set value and close the switch if the current falls below that value. Comparison of the measured and reference currents is preferably made at a frequency of, say, 50 to 200 kHz ie every 5-20 $\mu s$. The reference current may be supplied to the comparator from memory via a digital-analog converter.

The same circuit may, in principle, be used to generate the current in all the discrete time intervals in the duration of the spark. However, in practice it is customary for the spark to include an initial portion of relatively high amplitude, typically 200A, and a subsequent part with amplitude typically an order of magnitude lower. The first portion is mainly responsible for vapourisation of the sample, and the second portion for the emission of spectral light. In view of the widely differing amplitudes of these two portions of the spark, it is convenient to provide separate circuits for their generation. The two circuits may be qualitatively similar but will differ in the values of the various electrical components. Both circuits may be connected to the same power supply.

The circuit used to generate the initial, high amplitude portion of the spark is preferably such as to give a current amplitude of 200-300A within a rise time of less than 10 $\mu s$, more preferably about 5 $\mu s$.

For certain specialised applications in which such high current amplitudes are not required, the entire spark may be generated by the circuit used for the lower energy portion of the spark.

In conventional spark generators, the spark is initiated by the application of a high voltage in parallel with the spark gap. In a particularly preferred embodiment of the present invention, we provide a transformer to initiate the spark by generating a high voltage across, and in series with, the spark gap. This arrangement has very considerable advantages, notably the fact that the high voltage is applied only across the transformer and the spark gap which reduces or eliminates the need to protect other parts of the circuit from the effects of the high voltage. Also, there is a very short delay between initiation and the beginning of the spark. In fact, this delay may be negligible which eliminates the need for detection of the onset of the spark, timing being based on initiation. In addition, the system may be made very compact and, as a solid state system, virtually maintenance free.

A further advantage of the spark generator according to the invention is that it enables the calibration of the spectrometer to be greatly simplified in that the amount of sample vapourised can be made substantially independent of such physical properties of the sample as hardness, electrical and thermal conductivity, and melting point.

This is achieved by the provision of a feedback system which measures the intensity of spectral light emitted following a spark with an initial portion of a given amplitude, compares the measured intensity with a standard value and adjusts the amplitude of the initial portion so as to match the measured and standard intensities. The matching of the two intensities may be iterative. Throughout this procedure, the form and amplitude of the second portion of the spark are maintained constant.

According to a further aspect of the invention, there is thus provided a calibration system for an optical emission spectrometer, which system comprises
  a) a spark generator capable of generating a spark including an initial current pulse of programmable amplitude,
  b) a detector capable of measuring the intensity of spectral light emitted by a sample, and
  c) a feedback system capable of comparing the measured intensity with a standard value and adjusting the amplitude of the current pulse so as to match the measured and standard intensities.

Similarly, there is provided a method of calibrating an optical emission spectrometer, which method comprises
  a) exciting the atoms in a sample by passing through the sample a spark including an initial current pulse of known amplitude,
  b) measuring the intensity of spectral light emitted by the sample,
  c) comparing the measured intensity with a standard value, and
  d) adjusting the amplitude of the current pulse so as to match the measured and standard intensities.

In the especially favourable case where the samples under examination contain an approximately constant level of a particular element (as is the case, for example, in low alloy steels and carbon steels which contain approximately 97% iron) then the spectral light measured during the calibration process is preferably the light associated with that element. In the less favoured case, where no single element is present in a nearly constant proportion, the measured spectral light is preferably the sum of the light due to all the major elements present.

Another advantage of the present invention is based on the finding that the reproducibility or repeatability of intensity measurements depends at least in part on the presence of variable amounts of contaminants in the stream of argon gas which is generally used to flush the region of sparking. These contaminants, which may include methane and nitrogen, contain elements also present in the sample under investigation. Using the spark generator of the invention, we have devised a method of compensating for the presence of such contaminants, which comprises the steps of
  a) exciting a sample with a spark comprising a first portion having a current sufficiently high to vaporise the sample and a second portion of lower current,
  b) measuring a first intensity of light emitted during a time window located within the second portion,
  c) exciting the sample with a spark wherein the current in the first portion of the spark is insufficient to vaporise the sample, and
  d) measuring a second intensity of light emitted during the same time window.

Where the current in the first portion of the spark is sufficiently high to vaporise the sample, the emitted light contains contributions from the sample under investigation and also from any contaminants present in the atmosphere (eg methane present in the argon gas). Where the first portion of the spark is of lower current, no sample is vaporised and the emitted light is produced only by the contaminants. Subtraction of the second intensity from the first intensity gives the true value of the intensity du to the sample under investigation.

In order that the two measured intensities be comparable, it is necessary that, apart from the current of the first portion of the sparks, the measuring conditions under which the two intensities are measured be the same, ie the location of the time window with respect to the beginning of the spark and the magnitude of the current during the second portion of the spark. Using conventional spark generators it is not possible to vary the amplitudes of the two portions of the spark independently but with the present invention such independent control of the high and low amplitude parts of the spark is possible.

The above method of correction for the presence of contaminants in the stream of argon gas involves the use of so-called "time-resolved spectroscopy" ie to light being measured only within a specific time window located during one part of the spark. The use of time-resolved spectroscopy leads to particular advantages when used in conjunction with the spark generator of the present invention. For example, when a number of elements are to be determined simultaneously, the optimum form of spark for each will generally be different. Using conventional spark generators it is not possible to vary the form of the sparks used in a single measurement. Instead, a standard (sub-optimal) form of spark is used for all elements.

Using the spark generator of the present invention, on the other hand, each series of sparks may contain several different kinds of spark. In the simple case in which two different elements are determined, for example, the optimum spark for one may be relatively long-lasting, that for the other relatively short. A train of sparks having alternately the first and second form may be produced, the spectral light due to each being separately integrated by two measuring channels. Measurements of the two elements in a single train of sparks, rather than measuring the first element with one form of spark and then the second element with a second form of spark, is advantageous in that errors due to changes in the system between measurements are reduced or eliminated.

The advantages of this approach are refined still further by the use of time-resolved spectroscopy, since not only does the optimum form of the spark vary from one element to another but also the optimum location of the time window during which measurement is made. Thus, in the example described above in which two different forms of spark are alternated two corresponding measurement windows may also be alternated.

The use of time-resolved spectroscopy is advantageous in that, by appropriate manipulation of the data obtained, the quality of the spectral light (ie the spectral light to background ratio) can be improved several-fold in comparison with conventional detectors. This in turn improves the detection limit of the system and enhances the usefulness of the system in the detection of trace elements.

It is preferably possible for the use to define independently the number of time windows occurring within the duration of each spark, the positions of those windows with respect to the beginning of the spark and the duration of the windows.

The means for recording the intensities of light emitted during the time windows will generally be of conventional design. It may, for example, include a photomultiplier tube, an integrator and a sample-and-hold signal generator connected to an analog-to-digital converter.

We have found it to be advantageous not, as is customary, to measure the integrated intensity of light emitted after repeated sparking, eg of 1000 sparks, but to store the individual data points. This enables a measure of the confidence level, eg the relative standard deviation, to be calculated which may be used to assess whether or not a repeat measurement can be dispensed with. If it can, savings of time are achieved which may be very significant, especially in process control applications.

Analogous measurements may also be made where the light source is not a series of spark discharges but a continuous source, eg a plasma.

According to a further aspect of the invention, therefore, there is provided a method of optical emission spectroscopy which comprises sampling and separately storing the intensities of light emitted by a source during a large number of discrete time windows set during the overall emission of light by the source.

In a subsequent step, the variation of separate light intensities may be assessed, eg by calculating the relative standard deviation.

A similar method may be used to minimise the "pre-integration time" during which sparking occurs but no measurements are made. Typically the intensity of emitted spectral light increases during the pre-integration time to a steady value. The detection of this steady signal may be used as an indication that measurement may begin. This may result in time savings of several seconds, which may be of great significance in process control applications.

Large variations in the measured signal may also be taken as an indication that the sample is defective. Early recognition of this may again lead to valuable time savings.

Another problem addressed by the present invention is the fact that the determination of elements present only in trace amounts is limited by the so-called background radiation or, more accurately, by the variation of this background. Indeed, at trace levels, the intensity of the spectral line is often much lower than the intensity of the background. Variation of the background from measurement to measurement on the same sample limits the precision of the determination; variation of the background from one sample to another limits the accuracy.

Various methods have been used in attempts to overcome this problem. These methods are all based on the measurement of the background at a wavelength close to but outside the spectral line of interest. Such methods therefore involve either measuring the intensity of line plus background at the line wavelength and then the intensity of background only at a slightly different wavelength using the same spectrometer measuring channel, or using two independent measuring channels simultaneously, one for the spectral line and the other for the background determination. The former method involves doubling of the measuring time, and the need to find a wavelength with no other spectral line close to the line of interest (so as not to interfere with the background determination). The second approach suffers from the disadvantages of substantially higher cost (due to the need to provide a second measuring channel) and the problem of long term drift between the channels. Also, there is again the problem of finding a suitable wavelength at which to measure the background.

Using the techniques described above, we have devised a method of background correction for us in optical emission spectroscopy which involves measurement at only one wavelength using only one measurement channel. This method comprises comparing
 a) the intensity of light emitted during a portion of the duration of the spark in which the emitted light comprises substantially only background, and
 b) the intensity of light emitted during a portion of the duration of the spark in which the emitted light comprises background and spectral light.

We have found that, in a typical spark discharge, a portion of the duration of the spark in which the emitted light comprises essentially only background is the period in which the intensity rises. This period typically lasts about 30 $\mu$s.

In the subsequent period (typically 30–200 $\mu$s) the emitted light comprises both spectral light and background.

Thus, according to a specific aspect of the invention, there is provided a method of background correction in optical emission spectroscopy, which method comprises
 a) measuring the intensity of light emitted during the first 30 $\mu$s of a critically damped exciting spark (the first intensity),
 b) measuring the intensity of light emitted during the period of 30–200 $\mu$s from the beginning of the spark (the second intensity), and
 c) calculating a background correction factor based on the first and second intensities.

The correction factor may be a function of a number of variables, eg the wavelength, the concentration of the element under analysis and the durations of the two time windows in which measurements are made. However, in many cases, we have found that the ratio of the first intensity to the second intensity is substantially constant for a given wavelength. Thus, once the ratio has been determined for that wavelength, the background correction can be simply made. For example, the ratio R of the second intensity to the first intensity may be determined for a sample which does not contain any element which emits at the wavelength under examination. Then, if the measured first intensity for a sample which does contain such an element is $I_1$ and the measured second intensity is $I_2$, the spectral light contribution to the second intensity is $$I_2 - (I_1 \times R)$$

The above method of background correction is advantageous in that it requires no increase in the overall measurement time, nor does it require the provision of a second measuring channel in the spectrometer. In addition, the fact that the background is measured at the same wavelength as the line of interest compensates for any variation in background intensity with wavelength.

In principle, both the first and second intensities could be measured during appropriate time windows located within the same spark. However, this places considerable demands on the system hardware, notably the speed of the analog-to-digital converter, and increases the cost of the system accordingly. We prefer therefore that the measurements of the first and second intensities be made on alternate sparks in a series of sparks.

BRIEF DESCRIPTION OF THE DRAWINGS

The invention will now be illustrated, but in no way limited, by reference to the accompanying drawings in which.

DESCRIPTION OF PREFERRED EMBODIMENTS

Figure 1:
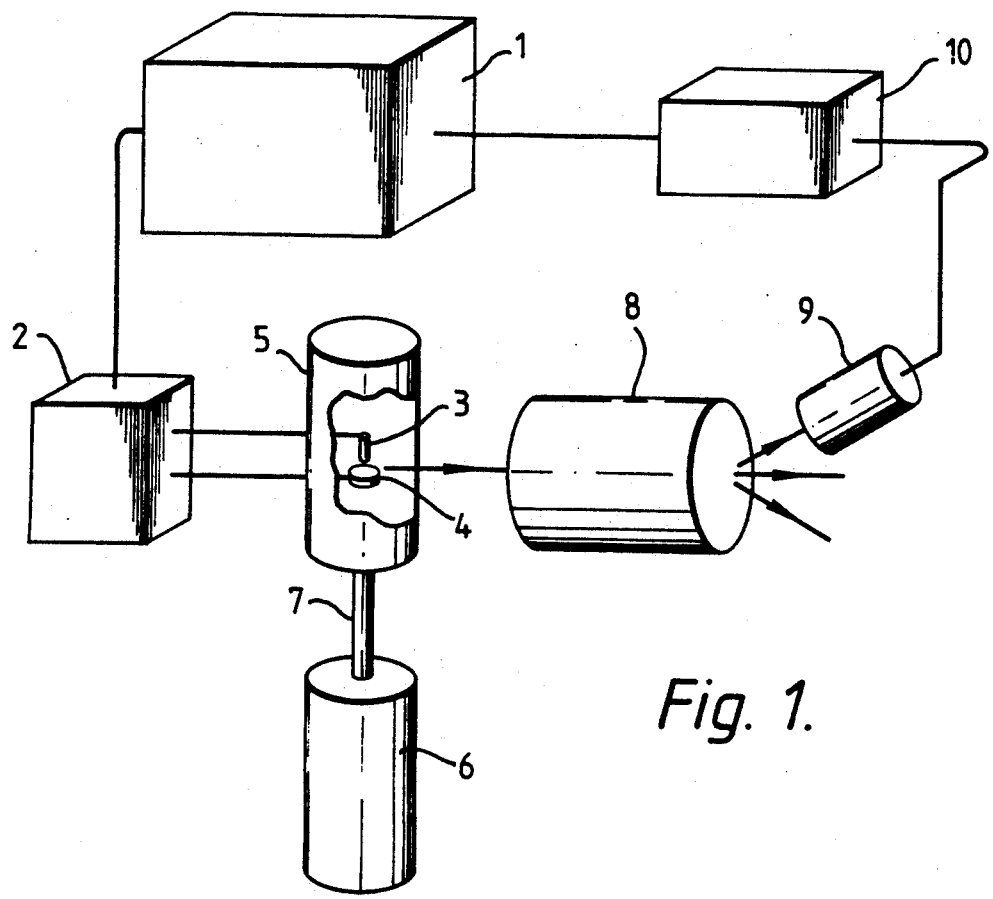
FIG. 1 is a schematic view of an optical emission spectrometer.

Referring first to FIG. 1, an optical emission spectrometer is controlled by a computer (1). The computer (1) controls a spark generator (2) which is connected to an electrode (3) and a sample (4) both of which are located in a sample chamber (5; shown partially cut away). The electrode is arranged close to the surface of the sample (4), which is in the form of a disc of metal, such that a spark gap exists between the tip of the electrode (3) and the sample (4). A container (6) of argon gas is connected to the sample chamber (5) by a pipe (7), the sample chamber (5) being flushed with argon during measurements.

When a spark of sufficient intensity is created in the spark gap the sample (4) is vapourised and thereby caused to emit light (shown by the arrowed lines) which is dispersed by an optical system (8) into discrete spectral lines. Light from one or more of the spectral lines is measured by a photomultiplier tube (PMT) (9).

The intensity of spectral light detected by the PMT (9) is measured by a light measuring system (10) and the results stored in the computer (1).

Figure 2A:
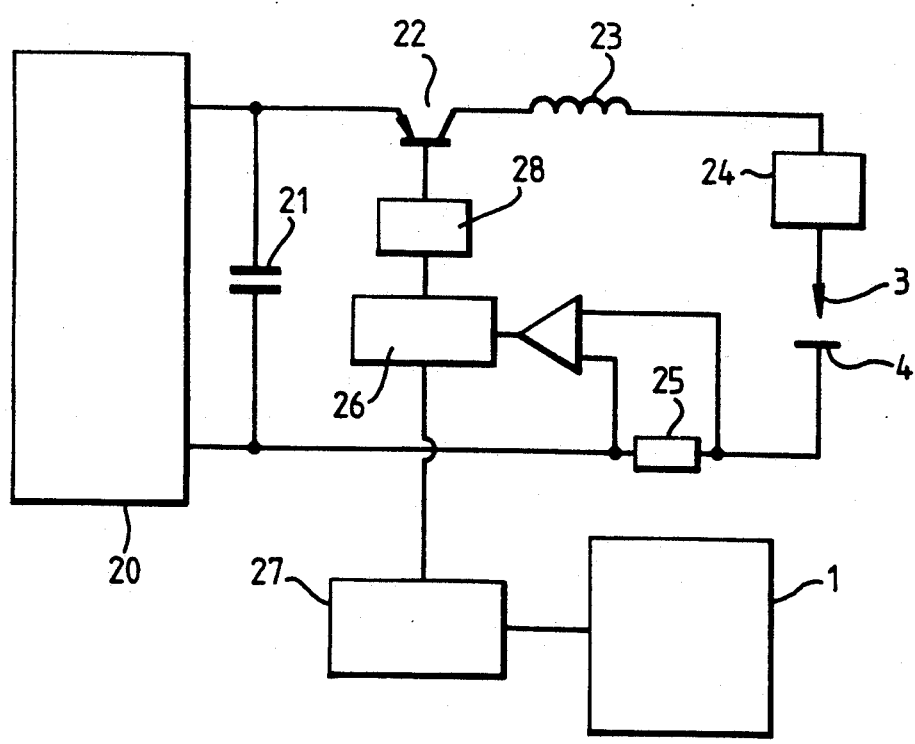
FIG. 2A is a schematic diagram of a spark generator forming part of the spectrometer of FIG. 1.

As is shown in FIG. 2A, the spark generator (2) comprises a 400V DC power supply (20) which charges a capacitor (21) and is connected via a transistor switch (22), an inductance (23) and an initiator (24) across a spark gap between the electrode (3) and the sample (4).

Current flowing through the spark gap is measured by means of a resistance (25) and comparator (26) which compares the measured current with a reference current supplied from the memory of the computer (1) via a digital-to-analog converter (27). Comparison of the measured and reference currents is made every 10 μs and the transistor switch (22) opened or closed by a driver (28) depending on whether or not the measured current is greater than or less than the reference value.

Figure 2B:
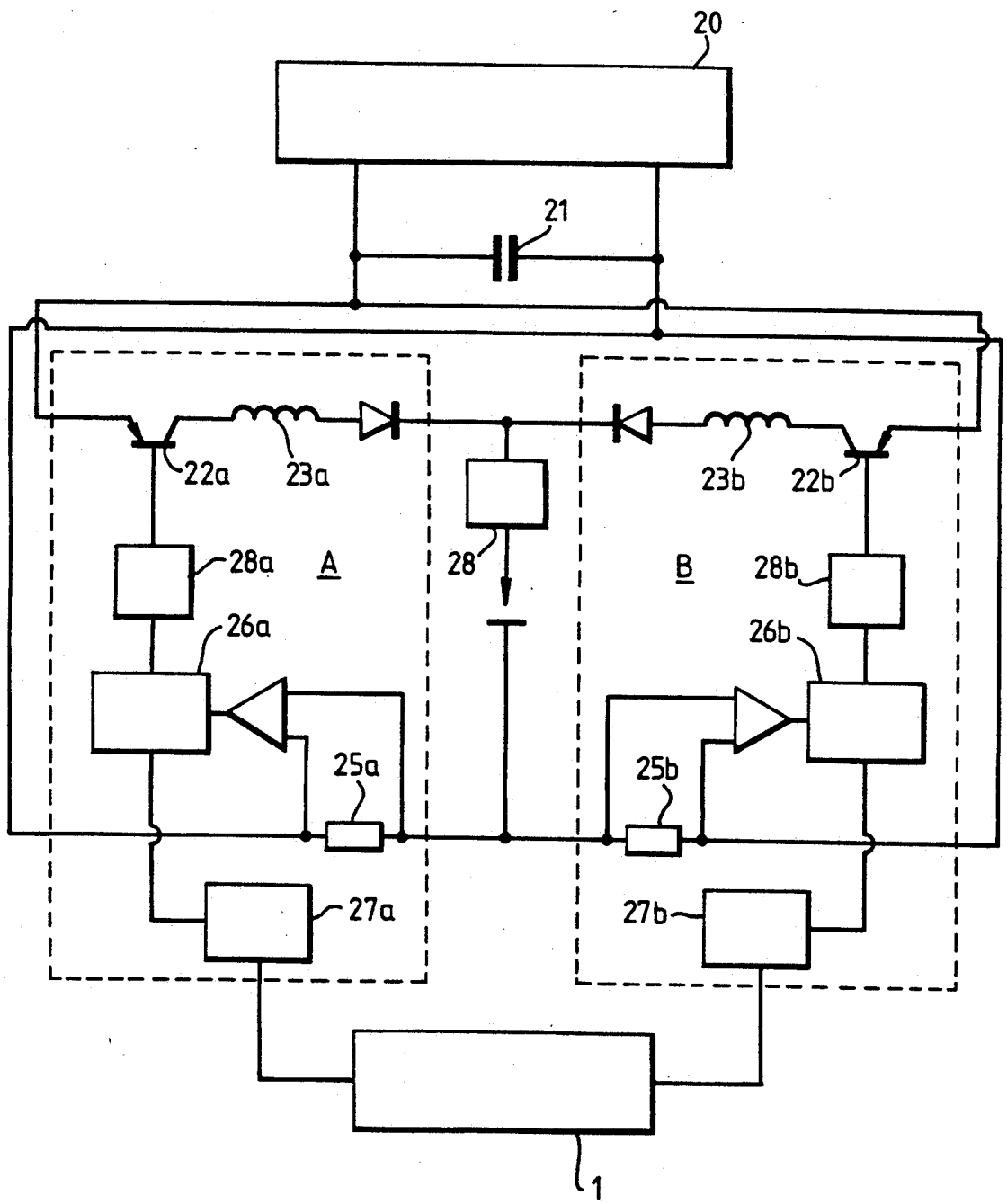
FIG. 2B shows a preferred refinement of the spark generator of FIG. 2A.

In the refinement shown in FIG. 2B, the power supply (20) is connected to two circuits, one (A) suitable for the generation of a relatively high amplitude current and the other (B) for the generation of lower current. In circuit A, the value of the inductance (23a) is 10 μH and the resistance (25a) is 5mOhm. In circuit B, the inductance (23b) is 100 μH and the resistance (25b) is 25mOhm. Two separate reference voltages are supplied to the comparators (26a,b) by separate digital-to-analog converters (27a,b).

Figure 3:
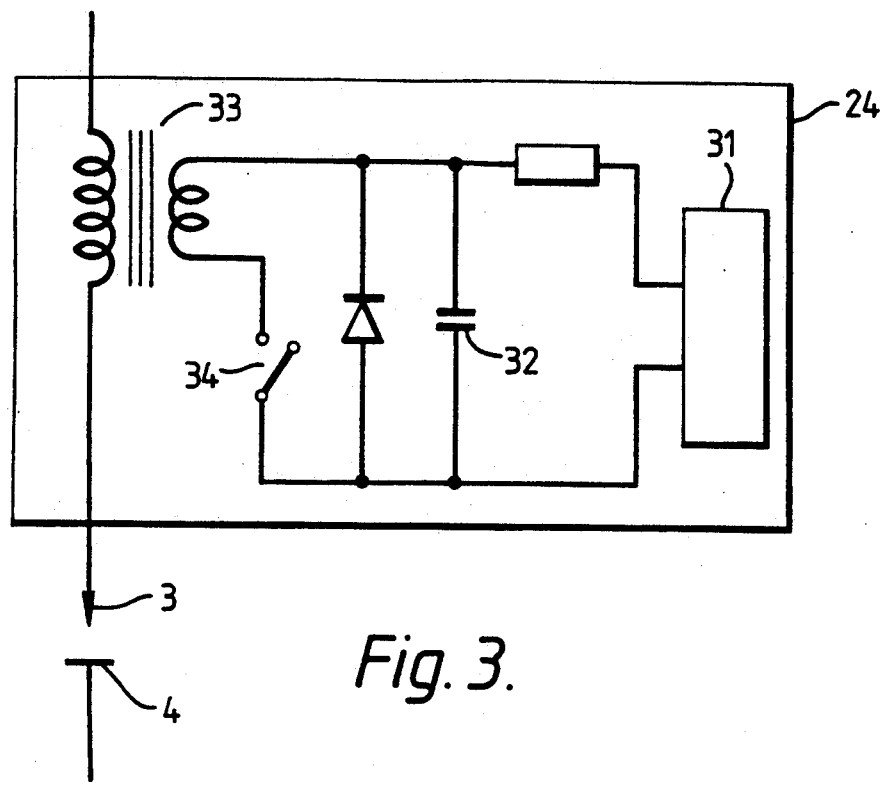
FIG. 3 is a schematic diagram of an initiator circuit forming part of the spark generator of FIG. 2.

A schematic diagram of the initiator (24) is shown in FIG. 3. This comprises a 1kV power supply (31) which charges a capacitor (32) and is connected across the primary coil of a transformer (33) with a primary:-secondary winding ratio of 1:12. When a switch (34) is closed, current flows in the primary coil of the transformer (33) thereby inducing a high voltage in the secondary coil and initiating a spark in the gap between the electrode (3) and the sample (4).

Figure 4:
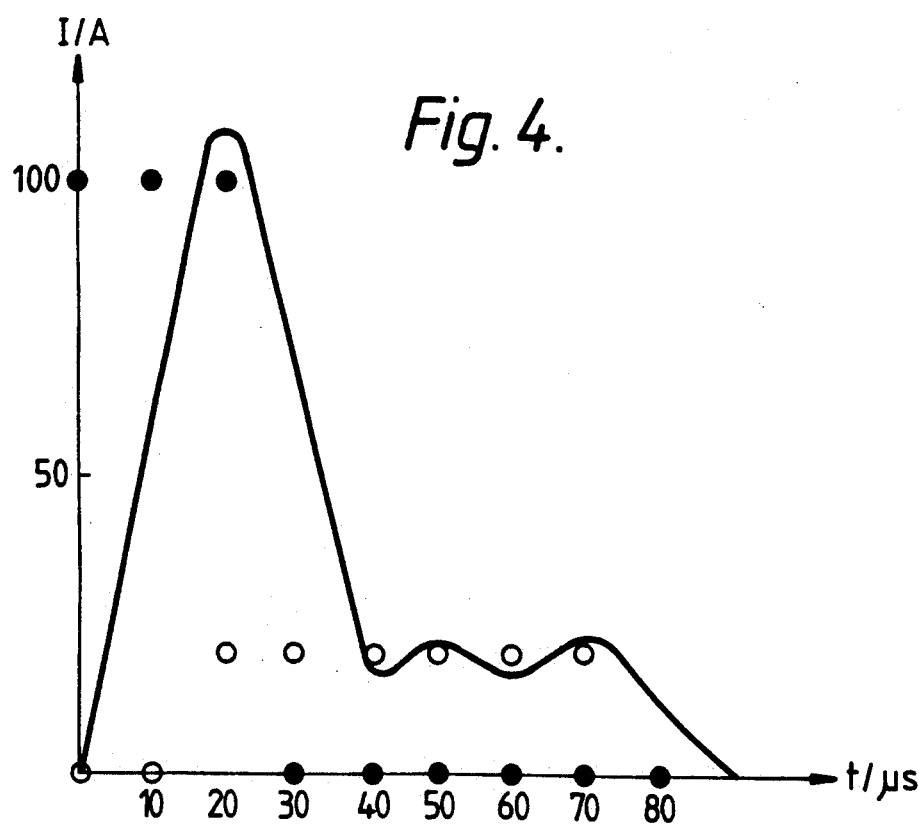
FIG. 4 shows a typical form of spark produced by the spark generator of FIG. 2.

A typical form of spark generated by the spark generator of FIG. 2A is shown in FIG. 4. In this diagram, the closed circles represent the values of the reference current for circuit A ($i_A$) and the open circles the reference current for circuit B ($i_B$).

Upon initiation of the spark, $i_B$ is zero and $i_A$ is 100V. The current flowing through circuit A therefore increases while that in circuit B is zero. At 10 μs the measured current is still less than $i_A$, the transistor switch (22a) remains closed and the current continues to rise. At 20 μs, however, the measured current is greater than both $i_A$ and $i_B$; the switch (22a) is opened and the current falls until at 40 μs the measured value is less than $i_B$ (20A). The switch (22b) in circuit B therefore closes and the current rises. At 50 μs, the measured current exceeds $i_B$ and the switch (22b) opens. The current continues to oscillate about $i_B$ until 80 μs when both $i_A$ and $i_B$ are zero.

Figure 5:
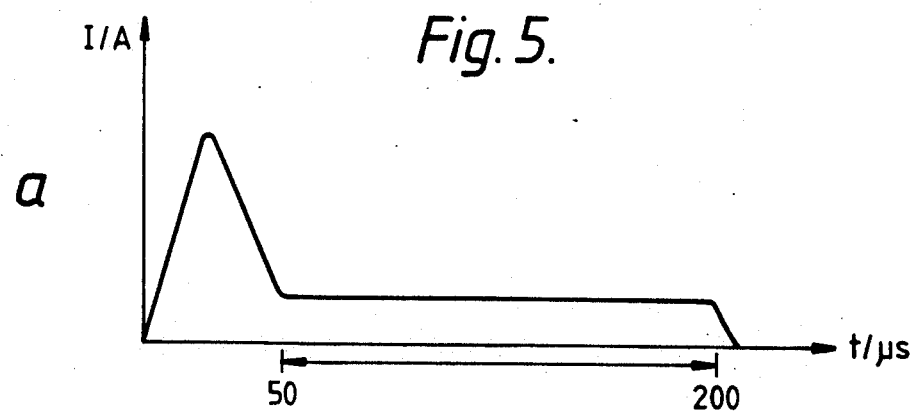
FIG. 5 shows forms of spark used in a method of correcting intensity measurements for errors introduced by the presence of contaminants.
Figure 5:
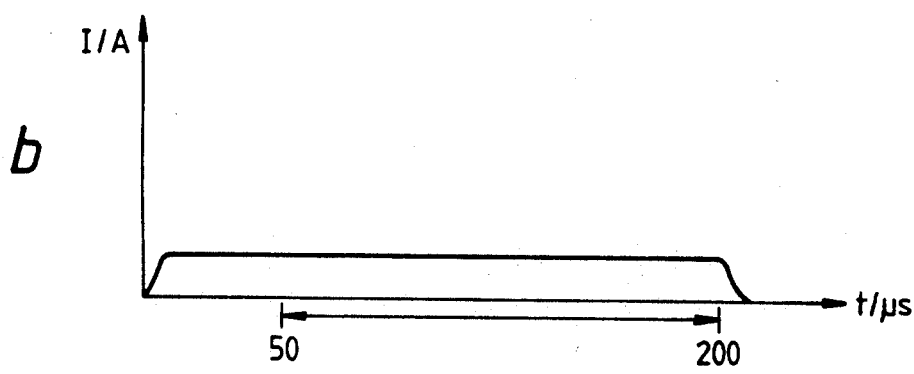
Figure 5:
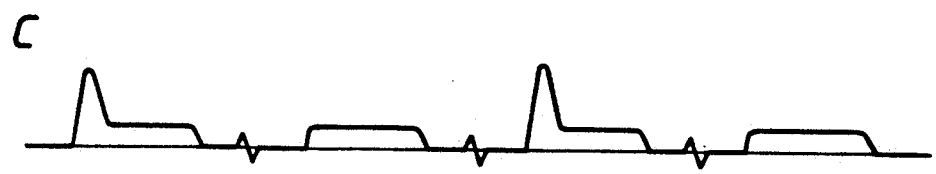

Referring now to FIG. 5, forms of a spark discharge are shown which are used in a method of correcting for errors introduced into a measurement by the presence of contaminants in the stream of argon gas used to flush the sample chamber during sparking. A first measurement is made using a spark having the form shown in FIG. 5a. This has a first portion, lasting about 30 μs, of high current, typically about 200A, followed by a second portion extending from 30 to 200 μs of much lower current, typically about 10A. The first portion of the discharge is of high enough energy to vapourise the sample under investigation, whilst the second portion is only strong enough to induce emission. The emitted light intensity is measured during a time window extending from 50 to 200 μs and contains contributions from the vapourised sample and any contaminants present.

A second measurement is then carried out using identical measuring conditions with the exception that the spark has constant amplitude throughout its duration, this being the amplitude of the second portion of the discharge used in the first measurement (see FIG. 5b). In this case no vapourisation of the sample occurs and the intensity of emitted light observed, again in the time window of 50 to 200 μs, is due entirely to contaminants. Subtraction of the second intensity from the first yields a corrected value for the intensity due to the sample in the first measurement.

As shown in FIG. 5c, the sparks of FIGS. 5a and 5b are conveniently applied alternately, the measured light intensities being integrated using separate measurement channels.

Figure 6:
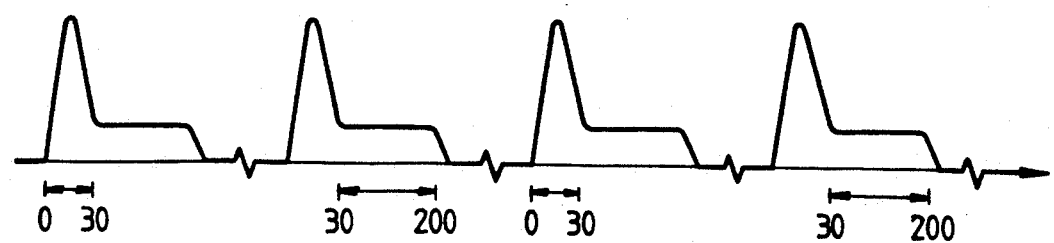
FIG. 6 shows forms of spark used in a method of background correction.

FIG. 6 shows a form of spark discharge used in a method of background correction as described above. Measurements are made during two time windows, the first beginning at the commencement of sparking and lasting 30 µs and the second beginning immediately after the first and extending to 200 µs from the beginning of the spark. Measurements are made first on a sample which is known not to contain any of the element which emits at the particular wavelength of light being detected. The measured light intensity therefore contains a contribution only from background. By way of illustration, say the measured intensity in the first time window is 1000 units and that in the second time window is 500 units. The ratio R of the second intensity to the first is therefore 0.5. If now a sample is measured which does contain the element under examination, the measured intensities in the two time windows may be, say, 980 and 495 respectively. Without background correction a lower intensity is found for the sample containing the element under examination than for the reference sample, due to slight (1% relative) differences in the (very strong) background radiation. Applying the method of the invention, however, the net line content of the second intensity is found to be $$495-(0.5\times980)=495-490=5$$

Figure 7:
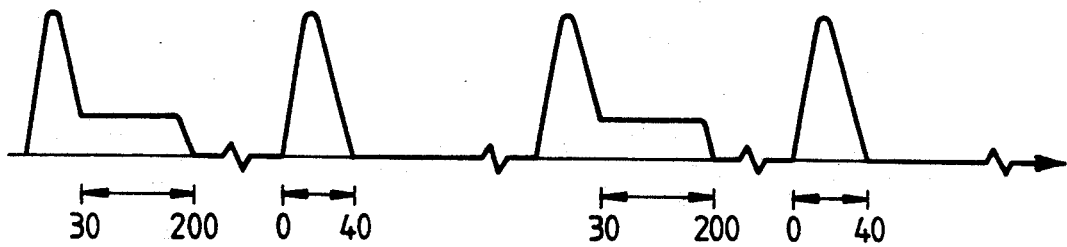
FIG. 7 shows forms of spark used in a method for the determination of two different elements in a sample.

FIG. 7 shows a sequence of sparks used in a determination of two different elements. For one element, a spark comprising an initial high current portion and a subsequent low energy portion is used, while for the other element the spark comprises only a high energy pulse. In the former case, the spectral light is measured during a time window located in the lower energy part of the spark, in the latter case, the light is integrated over the whole spark. The sparks are applied alternately and the emitted spectral light integrated using separate measurement channels.

Figure 8:
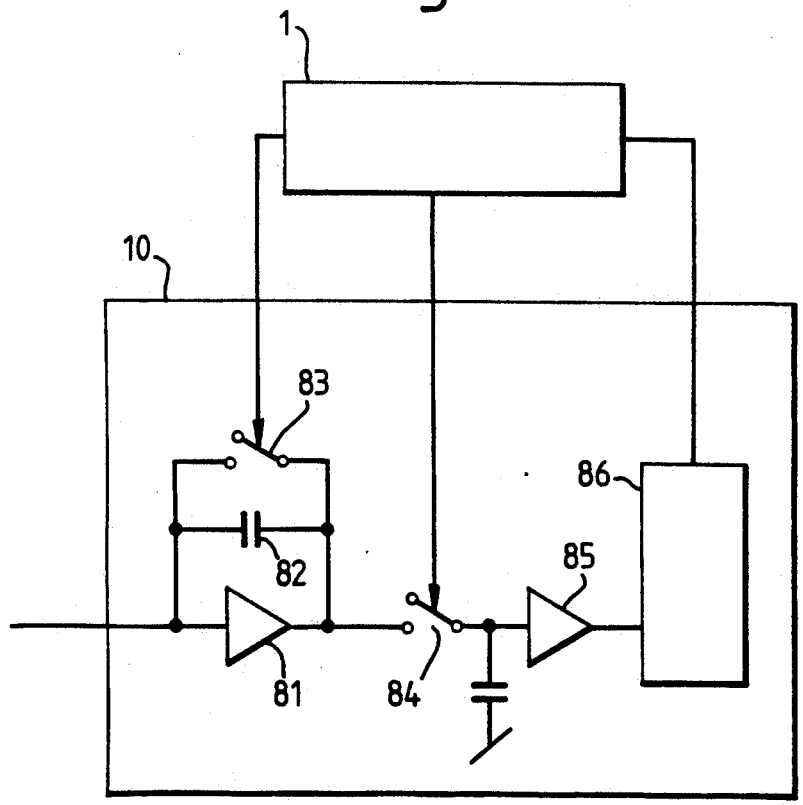
FIG. 8 shows a schematic diagram of light measuring system forming part of the spectrometer of FIG. 1.

The light measuring system (10) is shown in FIG. 8. It includes an integrator circuit comprising an operational amplifier (81) in parallel with a capacitor (82) and a switch (83). The integrator is separated by a switch (84) from a sample-and-hold circuit comprising a second operational amplifier (85). The sample-and-hold stores the value of an integrated signal long enough for it to be digitised by an analog-to-digital converter (86) which is in turn connected to the computer unit (1). Switches (83) and (84) are controlled by the timing system of computer (1).

In use, at the beginning of the measuring sequence, switch (83) is closed and switch (84) is open. The value of the integrated signal held by the integrator is zero.

Operation of the system will be illustrated for the case in which it is desired to measure the intensity of light emitted during a time window occurring at some predetermined time after initiation of the spark. At the beginning of the time window, the switch (83) is opened, thereby causing the intensity of the emitted light to be accumulated by the integrator. At the end of the time window, the switch (84) is closed causing the instantaneous value of the integrated intensity to be held by the sample-and-hold. The switch (84) is then again opened, and the switch (83) closed to return the value of the integrated intensity in the integrator to zero. The value of the intensity held by the sample-and-hold circuit is digitised by the ADC (86).

If the intensity of light emitted during a second time window is to be measured, then at the beginning of that window, the switch (23) is again opened and, at the end of the second time window, the switch (24) momentarily closed to transfer the second integrated intensity to the sample-and-hold circuit.

We claim:

1. A spark generator suitable for use in an optical emission spectrometer comprising:
   means for generating in a spark gap formed between an electrode and a sample to be analyzed a spark of a duration which extends over a series of discrete time intervals and which results in the flow of a current of programmable amplitude;
   means for measuring said current during at least one of said discrete time intervals;
   means for comparing said measured current with a reference current; and
   means for adjusting said measured current to a predetermined value dependent on said reference current.

2. A spark generator as claimed in claim 1 further comprising:
   first circuit means for generating in said spark an initial current pulse of relatively high amplitude; and
   second circuit means for generating in said spark a current of relatively low amplitude.

3. A spark generator as claimed in claim 1 wherein said discrete time periods during which said current is measured are between 5 and 20 micro-seconds.

4. A spark generator as claimed in claim 1 wherein the value of said reference current is stored in the memory of a computer unit.

5. A spark generator as claimed in claim 1 wherein said means for adjusting said current comprises a comparator and a transistor switch.

6. A spark generator as claimed in claim 1 which further comprises programming means for defining the form of a desired spark discharge.

7. A spark generator as claimed in claim 1 wherein the comparison of said current with said reference current is made at a frequency of 50-200 kHz.

8. A spark generator as claimed in claim 1 wherein said spark is initiated by application across said spark gap of a high voltage derived from a transformer connected in series with said spark gap.

9. An optical emission spectrometer comprising:
   a spark generator as claimed in claim 1;
   an optical system for dispersing light emitted by said sample; and
   light detection means for measuring the intensity of at least some of said light after it has been dispersed.

10. An optical emission spectrometer as claimed in claim 9 further comprising means for generating a series of sparks and a feedback system which measures the intensity of the light emitted by said sample following a first spark with an initial portion of a given amplitude and adjusts the amplitude of the initial portions of subsequent sparks comprised in said series so as to match the intensity of light emitted during those sparks with the intensity emitted during said first spark.

11. A method of optical emission spectroscopy comprising generating light for spectral analysis by a spark formed in a spark gap between an electrode and a sample to be analyzed, said spark having a duration extending over a series of discrete time intervals and resulting in a flow of current of programmable amplitude, said method further comprising the steps of:

measuring said current during at least one of said discrete time intervals;

comparing said measured current with a reference current; and adjusting said measured current to a predetermined value according to the value of said reference current.

12. A method of optical emission spectroscopy as claimed in claim 11 wherein said spark comprises an initial portion during which flows a current pulse of relatively high amplitude and a second portion during which flows a current of relatively low amplitude.

13. A method of optical emission spectroscopy as claimed in claim 12 wherein a series of sparks is generated and the light emitted during a large number of the discrete time windows contained in each of said sparks is integrated, said integrated value of each spark in said series of sparks being separately stored and evaluate.

14. A method of optical emission spectroscopy as claimed in claim 11 further comprising the steps of:

generating a first spark having an initial portion during which flows a current of sufficient amplitude to vaporize said sample and a second portion during which flows a current of relatively low amplitude;

measuring a first intensity of light emitted during a time window located in the second portion of said first spark;

generating a second spark during the entirety of which the current is insufficient to vaporize said sample; and measuring a second intensity of light emitted during the same time window in said second spark.

15. A method of optical emission spectroscopy as claimed in claim 11 further comprising the steps of:

measuring a first intensity of light emitted during a portion of a spark in which the light comprises substantially only background;

measuring a second intensity of light emitted during a portion of a spark in which the light comprises both background and the spectral light emitted by the sample; and correcting said second intensity for the contribution of background on the basis of the measurement of said first intensity.

16. A method of optical emission spectroscopy as claimed in claim 15 wherein the measurement of said first intensity is made during the first 30 micro-seconds of a critically damped exciting spark and the measurement of said second intensity is made during the period of 30–200 micro-seconds from the beginning of a spark.

17. A method of optical emission spectroscopy as claimed in claim 16 wherein the measurements of said first and said second intensities, respectively, are made on alternate sparks in a series of sparks.

* * * * *